(12) United States Patent
Muñoz

(10) Patent No.: US 9,168,319 B2
(45) Date of Patent: Oct. 27, 2015

(54) DEVICE AND PROCEDURE FOR CONTINUOUS TREATMENT OF WASTE

(75) Inventor: Javier De La Fuente Muñoz, Murcia (ES)

(73) Assignee: ECOHISPANICA I MAS D MEDIOAMBIENTAL S.L., Madrid (ES)

( * ) Notice: Subject to any disclaimer, the term of this patent is extended or adjusted under 35 U.S.C. 154(b) by 505 days.

(21) Appl. No.: 13/519,653

(22) PCT Filed: Dec. 30, 2009

(86) PCT No.: PCT/EP2009/009336
§ 371 (c)(1),
(2), (4) Date: Dec. 28, 2012

(87) PCT Pub. No.: WO2011/079853
PCT Pub. Date: Jul. 7, 2011

(65) Prior Publication Data
US 2013/0108506 A1     May 2, 2013

(51) Int. Cl.
*A61L 2/07*     (2006.01)
*A61L 11/00*    (2006.01)
*B09B 3/00*     (2006.01)

(52) U.S. Cl.
CPC . *A61L 2/07* (2013.01); *A61L 11/00* (2013.01); *B09B 3/00* (2013.01); *B09B 3/0075* (2013.01)

(58) Field of Classification Search
CPC ............. A61L 2/07; A61L 2/20; A61L 2/202; A61L 2/208
USPC .......................................................... 422/26
See application file for complete search history.

(56) References Cited

U.S. PATENT DOCUMENTS

| | | |
|---|---|---|
| 5,091,158 A | 2/1992 | Drauschke et al. |
| 5,427,650 A | 6/1995 | Holloway |
| 7,303,160 B2 | 12/2007 | Bouldin et al. |

FOREIGN PATENT DOCUMENTS

| | | |
|---|---|---|
| EP | 0870433 A1 | 10/1998 |
| GB | 2370242 A | 6/2002 |
| GB | 2452289 A | 3/2009 |

(Continued)

OTHER PUBLICATIONS

English machine translation of Hamada et al. JP 2004-003826. Jan. 8, 2004. Retrieved from Espacenet.*

(Continued)

*Primary Examiner* — Sean E Conley
*Assistant Examiner* — Donald Spamer
(74) *Attorney, Agent, or Firm* — Marshall, Gerstein & Borun LLP

(57) ABSTRACT

An apparatus and procedure for efficiently sterilizing waste material or products. The apparatus includes a reactor in the form of a cylindrical container housing two cylindrical tubes, a larger first tube and a smaller second tube. A first helical blade extends inwardly from the inner surface of the second tube, and a second helical blade bridges the outer surface of the second tube to the inner surface of the first tube. As the set of tubes is rotated in unison, material flows in one direction within the second tube and in the opposite direction in the space between the tubes. This axially compact design allows non stop introduction and extraction of waste, efficient use of heat energy, provided by steam injected into the reactor through a steam port, and allows for material to be input into and extracted from the device both at one end of the reactor.

9 Claims, 3 Drawing Sheets

(56) References Cited

FOREIGN PATENT DOCUMENTS

| | | |
|---|---|---|
| GB | 2456074 A | 7/2009 |
| JP | 2004003826 A | 1/2004 |
| WO | WO-03025101 A2 | 3/2003 |
| WO | WO-03026101 A1 | 3/2003 |
| WO | WO-2007079968 A2 | 7/2007 |
| WO | WO-2008010854 A1 | 1/2008 |
| WO | WO-2008065002 A2 | 6/2008 |

OTHER PUBLICATIONS

International Search Report of PCT/EP2009/009336 dated Oct. 7, 2010.

Notification of Reason for Refusal, Japanese Patent Office, application No. 2012-546364, dated Dec. 24, 2013.

Microfilm Utility Model Application 49-101486 (Publication of Utility Model 51-28351).

* cited by examiner

US 9,168,319 B2

DEVICE AND PROCEDURE FOR CONTINUOUS TREATMENT OF WASTE

CROSS-REFERENCE TO RELATED APPLICATION

The present application is the entry into the national phase and claims the benefit of priority of International Patent Application No. PCT/EP2009/009336, filed Dec. 30, 2009, which is incorporated herein by reference in the entirety.

BACKGROUND

1. Field of the Application

The procedure and device shown and described herein are for continuous sterilization of solid urban waste, livestock waste, agricultural waste and products, and food products. The waste or products are placed in a pressure tank, called the reactor, and submitted to certain elevated temperatures and pressures for a variable time depending on the material to be sterilized, such that the product is completely sterilized when taken out. Waste treated in this way is transformed and may be used subsequently.

2. Background

Closed-recipient stream-injection sterilization systems to sterilize medical waste, food products, woods, etc., are well-known. These systems are comprised of several phases: temperature and pressure increase, temperature maintenance for sterilization, cool-down, and decompression (removal of all internal steam).

Some of these systems are used to sterilize solid urban waste and home garbage. The organic material involved is transformed by the process and may be used again, once it is partially dried, to generate energy and even to manufacture products.

Generally cylindrical pressure tanks are used in this type of processes, and the waste in the tank is submitted to a certain temperature and pressure. Movement within the tank facilitates the separation of the materials and the extraction of the water they contain. For this reason, the processes already in use consist of several phases in the pressure tank. As we have said above:

Temperature increase phase
Temperature maintenance for sterilization phase
Cool-down phase
Decompression phase (elimination of all internal steam)

As part of the state of the art, the following documents are exemplary: U.S. Pat. No. 5,427,650; WO 03026101; WO 2007/079968; WO 2008/065002; WO 2008/010854; U.S. Pat. No. 7,303,160; WO 03/025101; EP 0 870 433; U.S. Pat. No. 5,091,158; GB 2,452,289; GB 2,456,074.

System of a company called Ambiensys S.L., as described in patent applications PCT/EP2006/012556, and PCT/EP2007/062353 process wastes in semi-continuous way by introducing limited quantities of waste by batches at various times during the process. This system also relies on gravity to remove processed material from the system.

The systems of the prior art have inherent problems arising from the periodic introduction of large quantities of waste to be sterilized in the pressure tank and/or the inefficiency in which the waste is handled. In batch processing, significant energy is wasted, since for each batch the tank must be pressurized, steam injected, temperature and pressure maintained for the time necessary for sterilization, the tank depressurized, and the batch of waste removed. Each of these phases inherently requires major energy consumption, besides prolonging the time necessary for processing each batch.

Apart from this, the processes used are rather complex to inject steam and to extract liquids while maintaining the pressure, temperature, and rotary movement within the pressure tank.

SUMMARY

In some aspects, the procedure and the apparatus described herein alleviate these problems by working in a continuous manner, avoiding the need for successive compressions and decompressions in the reactor each time materials to be sterilized are loaded or unloaded. This saves considerable time in the sterilization process and increases production, and saves a great deal of energy, since it reduces the consumption of fossil fuels for producing medium-pressure steam.

In some aspects, the devices shown and described herein are particularly suitable for continuous sterilization treatment of solid urban waste, stockbreeding waste, agricultural waste and products, assimilable industrial waste, and food waste and products.

In some aspects, the method disclosed herein is characterized by submitting any of the mentioned waste or products to a continuous treatment process, not by batches; that is, the waste is introduced uninterruptedly in the pressure tank, where treatment is time-regulated at temperatures of up to 170° C. and pressures of up to 7 bars.

In some aspects, the products or waste sterilized is removed uninterruptedly without the tank's interior losing pressure or temperature. This achieves the complete continuous cycle. The products or waste enters, is treated, and is removed continuously and not in batches or load units. This invention thus constitutes a new system in this market.

In some aspects, another characteristic is that the continuity of the process brings with it extraordinary savings in the energy consumption of the process.

In some aspects, the continuity of the process notably increases production capacity, since it completely avoids any dead time.

In some aspects, the disclosure introduces a device for sterilization treatment with characteristics which differentiate it from those already on the market.

Other aspects and advantages will be apparent upon review of the following description and appended claims.

DETAILED DESCRIPTION

Figure 1:
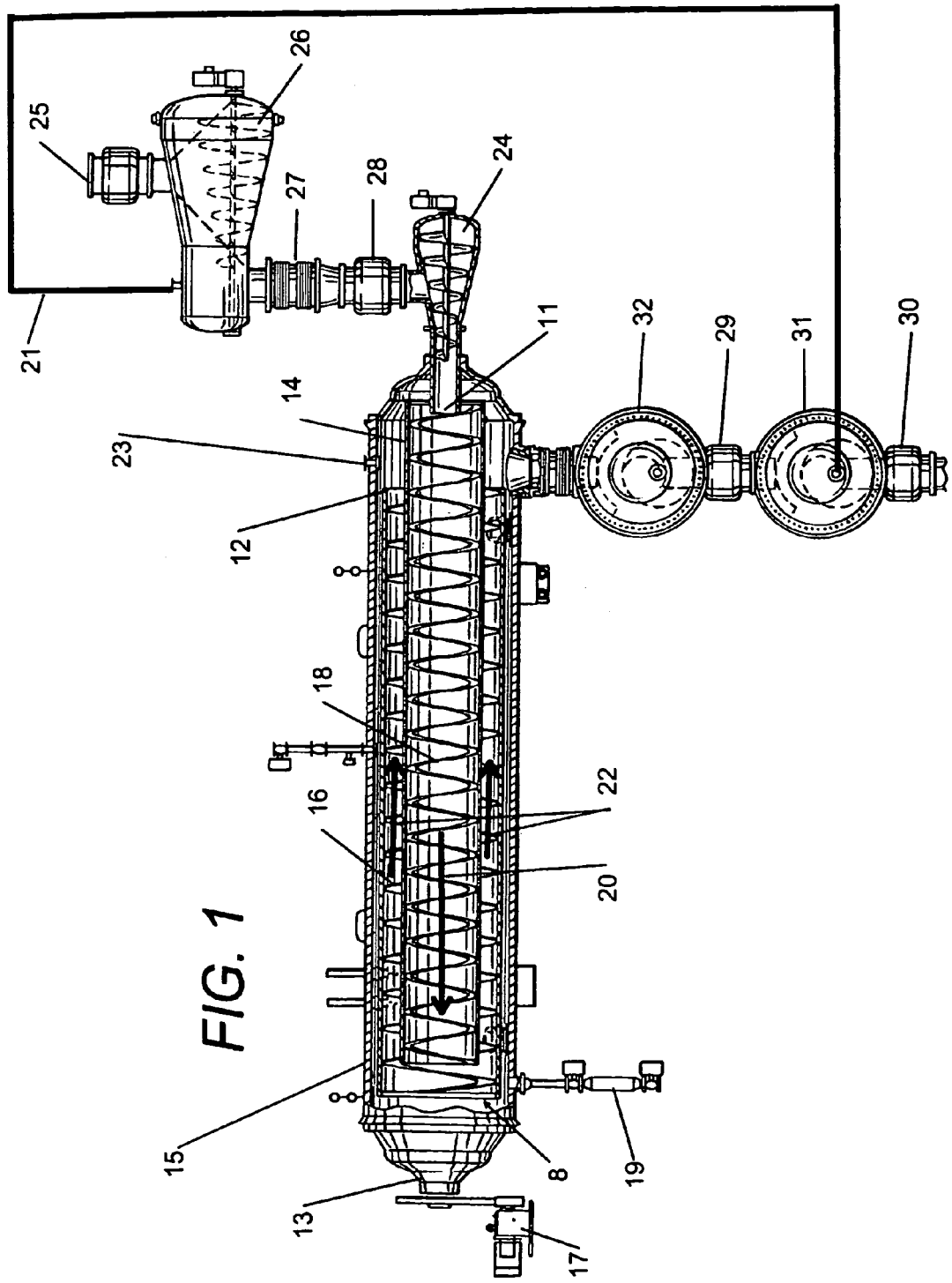
FIG. 1 is an elevational view, in partial section, illustrating a device that is an exemplary embodiment of the inventions shown and described herein.

In one arrangement, the apparatus shown and described herein includes a reactor, including a static external tank capable of containing the waste under pressure, and an internal rotating tank or reverse rotor which includes a first tube and a second tube, each of the first and second tubes being cylindrical and having a longitudinal axis, the first and second tubes being coaxial about their longitudinal axes, the first tube being larger in diameter than the second tube, an inner helical blade disposed on an inner wall of the second tube defining a first flow path for waste when the tubes are rotated about their longitudinal axes, an outer helical blade bridging an outer surface of the second tube and an inner surface of the first tube, the outer helical blade defining a second flow path for waste when the tubes are rotated about their longitudinal axes, the first and second flow paths being directionally opposite with respect to the longitudinal axes of said tubes, such that rotation of the tubes in rotational direction about its axis causes movement of waste in two axially opposite directions.

The first and second tubes are generally and preferably imperforate and form a "reverse rotor." The reverse rotor causes the waste materials or products introduced into the reactor move back and forth into the internal rotating tank, remaining inside in substantially continuous and uninterrupted movement for the time necessary to sterilize them. Because the reverse rotor has two flow paths, the time for sterilization is reduced in comparison with the systems in the prior art. The installation of this reverse rotor gives significant advantages on processes already on the market, namely: 1) significant energy savings over other systems on the market since the reverse rotor makes possible to shorten the length of the reactor and hence its weight, thus reducing the energy required for its rotary movement, 2) significant energy savings because the smaller size of the reactor means also smaller volume of the tank to pressurize thus reducing the consumption of steam, 3) significant energy savings because the reverse rotor also allows the application in a shorter time of the required pressure and required temperature in the area of input and extraction of waste or products, 4) significant energy savings by using the steam surplus through the deposits of compensation for input and extraction of waste or products, 5) significant increase in production compared to other systems on the market precisely because the smaller size of the reverse rotor makes a faster implementation of pressure and temperature in the area of entry and extraction of waste or products, 6) the reactor is smaller than those already on the market, and its operation and handling are simpler and less expensive to manufacture and maintain, and 7) the reverse rotor is arranged so that entrance to and exit from the reactor are close to each other, avoiding mechanical problems due to thermal expansion, since the motors and devices for the input and extraction of waste remain static and the flexible connections therefor consist of the joints for expansion at only one end of the reactor, which is where the entrance and exit are both located.

Another characteristic of apparatus shown and described herein is that the reactor has only one steam input, which is located in the area of input and extraction. This improves very much the initial movement of the products or waste into the internal rotating tank, obtaining a significant time savings in treatment as compared with other systems.

Another difference is that, in the reactor, internal rotating tank support mechanism is sits on wheels rolling on the inner wall of the external static tank. This ensures quick, simple maintenance and avoids having to send personnel into the reactor to do maintenance work. Thus, there is no contact between maintenance personnel and the waste.

The apparatus and procedure described herein include four compensation devices, two input devices synchronized with each other, and two extraction devices synchronized with each other. Also, the first input device and the second extraction device are synchronized with each other for purposes of utilization of steam surplus. These devices feed and remove waste into and out of the reactor. They function independently of the reactor itself; that is, the operation of the reverse rotor does not depend on signals from the input or extraction devices. This represents several advantages over all other existing systems. These advantages include: 1) the fact that the input and extraction devices have sufficient capacity so as to not require opening and closing of valves adjacent to the compensation deposits in time periods of less than five minutes, avoiding premature wear and tear on the mechanical elements, 2) the synchronization of the input an extraction devices with each other reduces energy consumption to one fifth that of method used in prior art systems, 3) the significant savings resulting from this system makes possible the recuperation of steam surplus which can be used for water treatment processes and also to generate cold air through absorption machine, and 4) unlike in other systems, there is no synchronization between the internal rotating tank of the reactor and compensation deposits to introduce and remove the materials to be sterilized, thus avoiding serious mechanical problems with the coupling of the materials introduced, especially solid urban waste, could cause.

To summarize, the apparatus and procedure described herein are based on the performance of the three main components, the reactor, the input devices and the extraction devices, which operate simultaneously to carry out the described procedure.

Figure 2:
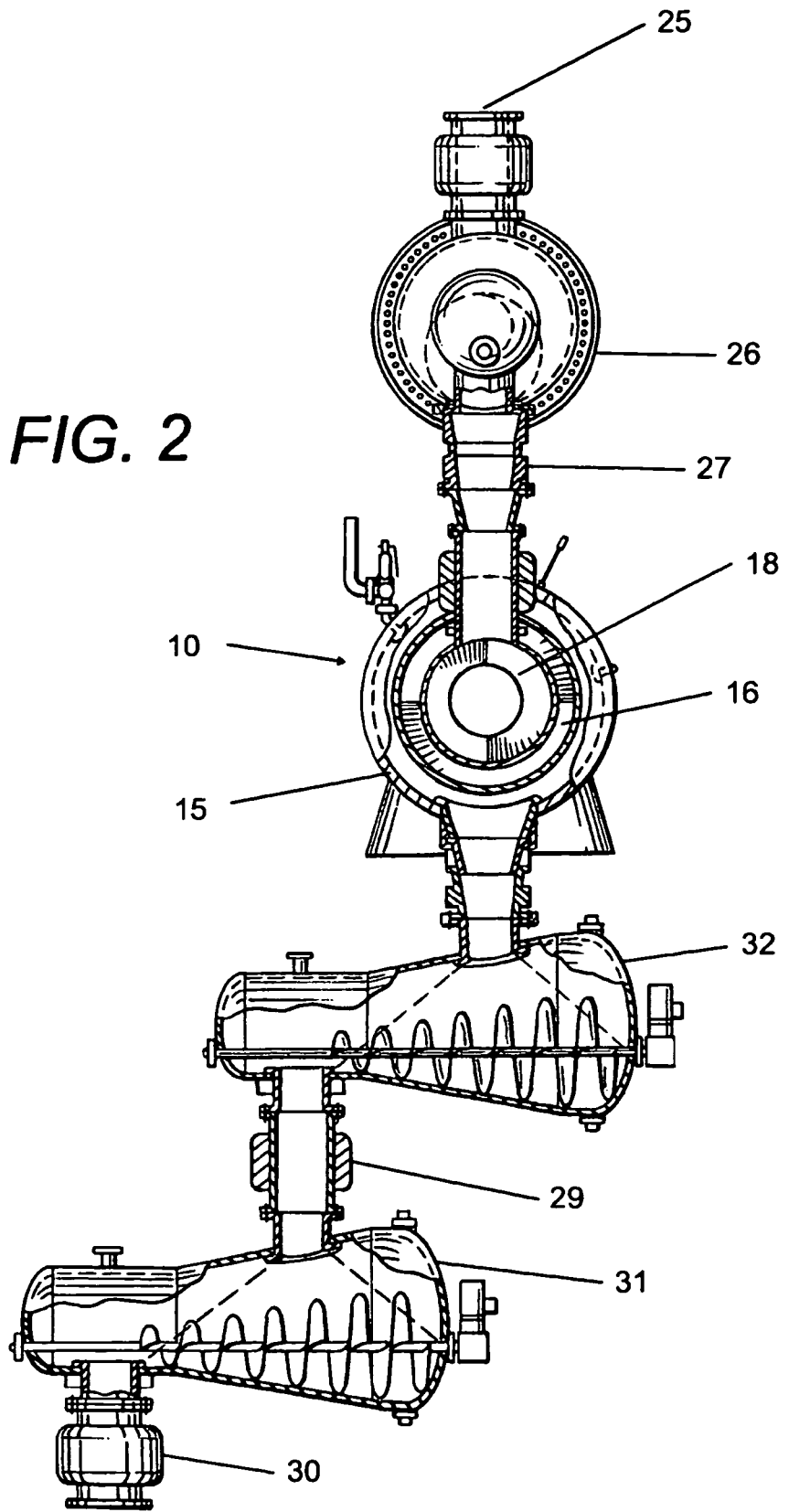
FIG. 2 is an end view, in partial section, of the device shown in FIG. 1.

FIGS. 1 and 2 show a reactor 10 with a proximate end 11 and a distal end 13. The reactor 10 is comprised of an external static tank 15 that houses or contains two concentric cylindrical tubes 12 and 14. Two oppositely oriented helical blades, 16 and 18, push waste back and forth through the reactor 10 in opposite directions, based on rotation of the tubes in one rotational direction. The inside surface of the outer or larger first tube 12 is joined to the outside surface of the smaller second tube 14 by the first helical blade 16 that bridges the space between the tubes 12 and 14. The first helical blade 16 is welded to the inside surface of the tube 12 and the outside surface of the tube 14 The second helical blade 18 is welded to and extends inwardly from, in a cantilevered manner, the inside surface of the second tube 14. The first helical blade 16 is oriented such that it pushes waste axially in an axial direction 22 toward the proximate end 11 of the reactor when the tubes 12 and 14 are rotating, and the second helical blade 18 is oriented such that the same rotational movement of the tubes causes waste to move through the second smaller tube 14 in the opposite axial direction 20 toward the distal end 13 of the reactor 10. Thus, the tubes 12 and 14 and the oppositely oriented helical blades 16 and 18 create a rigid unit called a reverse rotor 8 that pushes waste both back and forth inside the reactor 10. The reverse rotor 8 rotates when the main, preferably single, motor 17 produces the rotation of the tubes 12 and 14, which move in the same rotational direction, and which are joined by helical blade 16 causing the tubes to rotate in unison.

Figure 3:
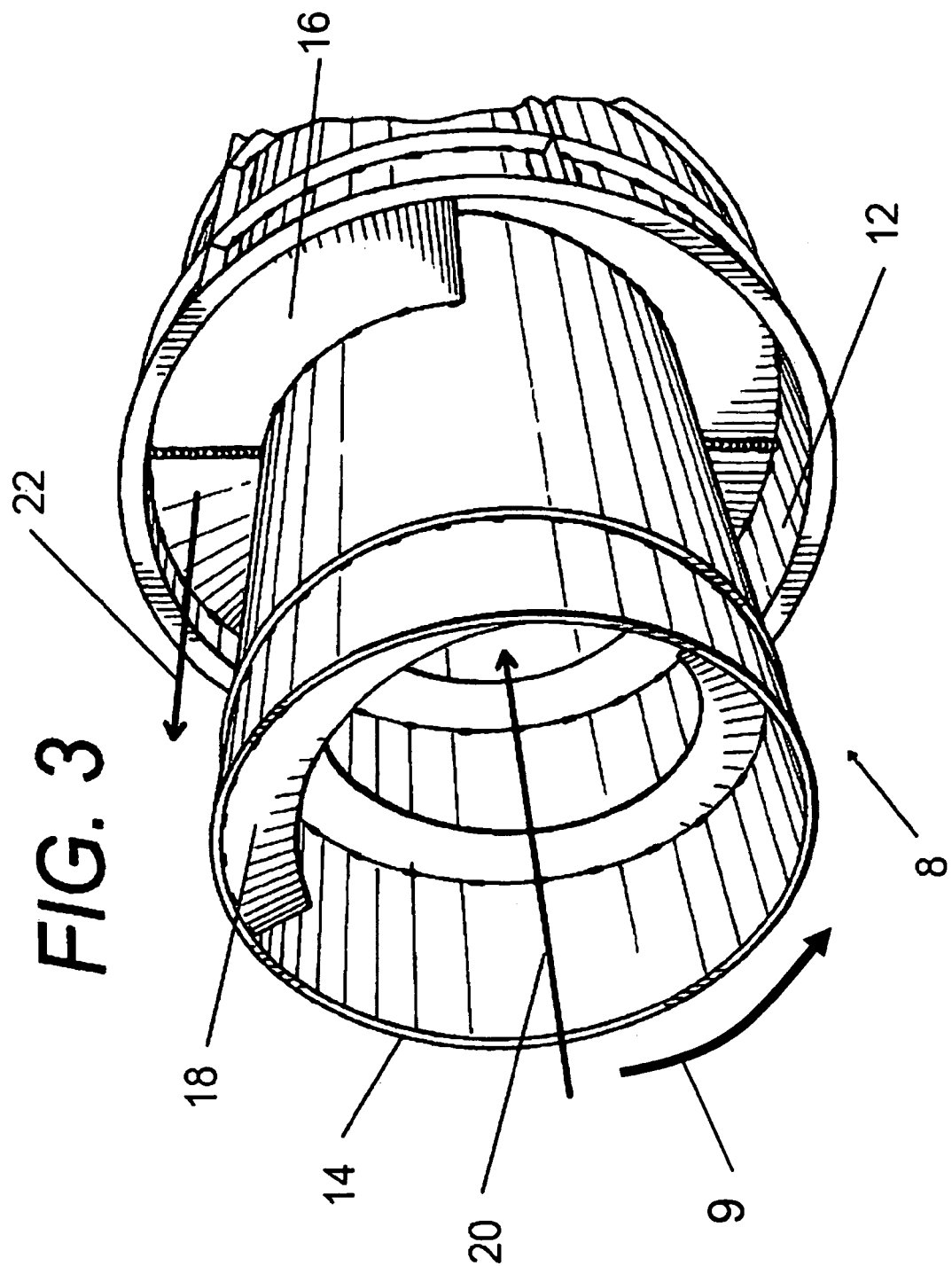
FIG. 3 is an enlarged perspective view of the proximal end of the interior components of the device shown in FIG. 1.

FIG. 3 is an enlarged perspective view of the proximal end of the reverse rotor 8. The blade 16 is rigidly connected (for example, by welding) to the inside surface of the large tube 12 and to the outside surface of the smaller tube 14. The arrow 20 shows the first flow path and the arrow 22 shows the second flow path, and flow through both of these paths occurs at the same time and in opposite directions when the reverse rotor 8 is rotated in the direction of the arrow 9 in FIG. 3. The blade 18 and the blade 16 are configured to be opposite-handed to bring about this reverse flow.

Two input devices 24 and 26, each having an auger, are synchronized with each other to put waste into the reactor 10. The first input device 26 is located above the second input device 24, and connected to it by a flexible coupler 27. The input device 24 is connected to the first end 11 of the reactor. Each of the input devices, 24 and 26 has an input control valve, 28 and 25 upstream of the respective input device.

Similarly, waste is extracted from the reactor with two cooperating extraction devices 32 and 31 synchronized with each other, each of which has an auger inside, and each of which has an extraction control valve 29 and 30, downstream of its respective extraction device.

The pair of input devices 24 and 26 are synchronized with each other such that when the first input device 26 is opened to atmosphere to receive waste to be treated, the second input device 24, and its corresponding control valve 28, maintain the pressure inside the reactor 10. Similarly, when the second extraction device 31 is opened to atmosphere to expel treated waste, the first extraction device 32, and its corresponding control valve 29, maintain pressure inside the reactor 10.

The second or final extraction device 31 and the first input device 26 are connected by a steam compensation tube 21, which release surplus steam which may be gathered or directed (with valves not shown) for use in other processes like water purification or generation of cold air by absorption.

The reactor 10 is equipped with a steam input valve 23 located on top of the reactor-near the proximate end 11. At a distal end 13 of the reactor 10 the design of the helical blades allows waste to transfer from the first flow path 20 to the second flow path 22. Also near the distal end 13 of the reactor 10, a liquid or fluid extraction port 19 allows the removal of leachate and other flowable material carried by the leachate from the reactor 10.

Organic waste, paper and cardboard will decompose and is converted into a format somewhat similar to the kind of ground tobacco that is used in cigarettes. Organic matter absorbs a substantial amount of water in the process because of the condensation of steam.

Waste comprised of plastics, except PET, are typically reduced to ball-like masses, and other solid residue typically maintain their shape. After being treated the waste gets a reduction in volume of about a 70 percent. Air contained within the waste is released during the process through a release valve on the top of the reactor.

The reverse rotor comprised of the tubes 12 and 14 and the helical blades 16 and 18 moves at variable speed depending on type of waste or products to treat. For urban waste, reverse rotor typically moves at few rpm, enough to process up to 8 tons of municipal waste per hour. For other special non-urban waste or other products, the speed may be varied, as well as may be changed the pressure and/or the temperature. Each type of waste or product to be sterilized should be examined to see what will result in the sufficient treatment of the material being handled.

Metals and plastics can be extracted and recycled. The organic matter leaves the process mixed with paper and cardboard, and can have many applications for that: power generation, biogas, biodiesel, production of materials.

The sterilization process here described produces some surplus steam, and the steam is thermal energy that we can lead to its use in other processes such as water purification or cold air generation. The steam compensation tube 21, releases surplus steam through a valve and can be used in other processes.

Municipal Solid Waste (MSW), i.e., typical human garbage, may contain things like textiles and other things that could cause clogging, and have the potential to could damage internal mechanical elements within the reactor 10. Damage from such materials is minimized by forcing incoming waste through the two smaller input devices 24 and 26, which are much more accessible and easy to repair, as compared to the larger and more complex reactor 10.

Treated waste enters into the reactor through the input devices 26 and 24 in non-stop continuous process, and waste leaves the reactor through extraction devices, which will extract the treated waste through the second output deposit 31.

A typical preliminary step, not shown herein, entails the use of shredding machines that can regulate the desired size of the waste. Such pre-treatment avoids possible breakdowns into the reactor 10.

The device and procedure described herein is able to treat solid urban waste, stockbreeding waste, agricultural waste and products, assimilable industrial waste, and foods waste and products, and it is characterized by continuous operation rate of up to 8 tons per hour. Removal of the sterilized materials from the reactor occurs continuously and without interruption and with no need to decompress the reactor.

The procedure described above is characterized by the continuous entrance and exit of materials from the reactor 10 at a selected and adjustable temperature, pressure and speed, depending on the material being processed.

The foregoing describes inventions by referring to particular embodiments or examples. These embodiments are meant to be illustrative and not limiting. Many variations, modifications, additions, and improvements are possible, and will apparent to persons of skill in the relevant art. Accordingly, all apparent and not-so-apparent alternatives, modifications, additions, and improvements are intended to be encompassed within the following claims.

What is claimed is:
1. An apparatus for treating waste comprising:
a reactor comprising an external static tank capable of containing the waste under pressure, a reverse rotor disposed within the external static tank, the reverse rotor comprising a first tube and a second tube, each of the first and second tubes being cylindrical and having a longitudinal axis, the first and second tubes being coaxial about their longitudinal axes, the first tube being larger in diameter than the second tube, an inner helical blade disposed on an inner wall of said second tube defining a first flow path for waste when the reverse rotor is rotated about the longitudinal axes of the first and second tubes, an outer helical blade bridging an outer surface of the second tube and an inner surface of the first tube, the outer helical blade defining a second flow path for waste when the reverse rotor is rotated about the longitudinal axes of the first and second tubes, the first and second flow paths being directionally opposite with respect to the longitudinal axes of said tubes, such that rotation of the reverse rotor in the rotational direction about its axis causes movement of waste in two axially opposite directions, wherein the first and second tubes are joined together by the outer helical blade and rotate in the same rotational direction.
2. An apparatus in accordance with claim 1 wherein:
a first input device has an auger that directs waste into a second input device through an entry valve, the second input device has an auger that directs waste into one end of the reactor to introduce the waste into the second tube of the reverse rotor.
3. An apparatus in accordance with claim 1 wherein:
a first extraction device has an auger that moves waste from one end of the first tube through a first exit valve to a second extraction device, and wherein the second extraction device has an auger that expels waste from the second extraction device through a second exit valve.

4. An apparatus in accordance with claim 1 wherein:
a set of four wheels are mounted in the inner wall of the external static tank, wherein the reverse rotor is supported on the wheels for rotational movement within the reactor.

5. An apparatus in accordance with claim 1 wherein:
the reactor has a steam port through which steam may be introduced into the reactor at elevated temperature and pressure, and the reactor has an extraction port through which leached substances may be removed from the reactor.

6. An apparatus for treating waste comprising:
a pressurizable and cylindrical external static tank having a longitudinal axis, a proximate end, and a distal end, a reverse rotor disposed within the external static tank, the reverse rotor comprising a larger first tube and a smaller second tube joined together coaxially by a first helical blade, a second inner helical blade disposed on an inner wall of the second tube defining a first flow path for waste when the reverse rotor is rotated about its longitudinal axes, and the first helical blade defines a second flow path for waste when the reverse rotor is rotated about its longitudinal axes, the first and second flow paths being directionally opposite with respect to the longitudinal axes of the tubes, such that rotation of the reverse rotor about its axis causes movement of waste through the first flow path away from the proximate end of the reactor and toward the proximate end through the second flow path when the reverse rotor is rotated, wherein the first and second tubes rotate in the same rotational direction.

7. An apparatus in accordance with claim 6 wherein:
the reactor further comprises first and second input devices synchronized with each other, each with an auger, the first input device being arranged so as to direct waste into the second input device through an entry valve, and the second input device being arranged so as to direct waste into the proximate end of the reactor and into the first flow path.

8. An apparatus in accordance with claim 6 wherein:
the reactor further comprises first and second extraction devices, each with an auger, the first extraction device being arranged to move waste from the proximate end of the reactor to the second extraction device, the reactor further comprises a set of four wheels mounted in the inner wall of the external static tank, the reverse rotor being mounted on such rollers for rotational movement in the external static tank, the reactor further comprises a steam port through which steam may be introduced into the reactor at elevated temperature and pressure, and the reactor has a liquid extraction opening through which liquid substances may be removed from the reactor.

9. An apparatus for the treatment of waste comprising:
a pressurizable and cylindrical reactor having a longitudinal axis and a proximate end and a distal end, a reverse rotor disposed within the external static tank of the reactor and rotatable on bearings wheels carried within the inner wall of the external static tank, the reverse rotor comprising a larger first imperforate tube and a smaller second imperforate tube joined together coaxially along a second longitudinal axis by a first helical blade, a second inner helical blade disposed on an inner wall of the second tube defining a first flow path for waste when the reverse rotor is rotated, and the first helical blade defining a second flow path for waste when the reverse rotor is rotated about the second longitudinal axis, the first and second flow paths being directionally opposite with respect to the second longitudinal axis, such that rotation of the reverse rotor about the second longitudinal axis causes movement of waste through the first flow path away from the proximate end of the reactor and toward the proximate end through the second flow path when the reverse rotor is rotated, wherein the first and second tubes rotate in the same rotational direction; and the reactor further comprises first and second input devices synchronized with each other, each with an auger, the first input device being arranged so as to direct waste into the second input device though an entry valve, the second input device being arranged so as to direct waste into the proximate end of the reactor and into the first flow path; and the reactor further comprises first and second extraction devices synchronized with each other, each with an auger, the first extraction device being arranged to move waste from the proximate end of the reactor to the second extraction device, the reactor further comprises a set of four rollers mounted in the inner wall of the external static tank of the reactor, the reverse rotor being mounted rotatably on the rollers for movement within the external static tank, the reactor further comprises a steam port through which steam may be introduced into the external static tank at elevated temperature and pressure, and the reactor has a liquid extraction opening through which liquid substances may be removed from the external static tank, at least one of the input devices and at least one of the extraction devices cooperating with each other for purposes of utilization of steam surplus.

* * * * *